United States Patent
Kunst et al.

(10) Patent No.: US 9,115,246 B2
(45) Date of Patent: Aug. 25, 2015

(54) POLYETHER POLYOLS, PROCESS FOR PREPARING POLYETHER POLYOLS AND THEIR USE FOR PRODUCING POLYURETHANES

(75) Inventors: Andreas Kunst, Ludwigshafen (DE); Berend Eling, Lemfoerde (DE); Achim Loeffler, Speyer (DE); Heinz-Dieter Lutter, Lembruch (DE); Wei Han, Pudong (CN); Jens Mueller, Lohne (DE)

(73) Assignee: BASF SE, Ludwigshafen (DE)

( * ) Notice: Subject to any disclaimer, the term of this patent is extended or adjusted under 35 U.S.C. 154(b) by 323 days.

(21) Appl. No.: 13/092,469

(22) Filed: Apr. 22, 2011

(65) Prior Publication Data

US 2011/0269863 A1 Nov. 3, 2011

Related U.S. Application Data

(60) Provisional application No. 61/329,569, filed on Apr. 30, 2010.

(51) Int. Cl.
*C08G 65/26* (2006.01)
*C07C 69/34* (2006.01)
*C07C 69/52* (2006.01)
*C07C 69/734* (2006.01)
*C08G 18/10* (2006.01)
*C08G 18/40* (2006.01)
*C08G 18/48* (2006.01)
*C08G 101/00* (2006.01)

(52) U.S. Cl.
CPC ............ *C08G 65/2606* (2013.01); *C07C 69/34* (2013.01); *C07C 69/52* (2013.01); *C07C 69/734* (2013.01); *C08G 18/10* (2013.01); *C08G 18/4072* (2013.01); *C08G 18/4891* (2013.01); *C08G 65/2615* (2013.01); *C08G 65/2663* (2013.01); *C08G 2101/0008* (2013.01)

(58) Field of Classification Search
CPC ........... C08G 65/2606; C08G 65/2615; C08G 65/2663; C07C 69/34; C07C 69/52; C07C 69/734
USPC .................. 560/181, 182, 199, 200, 205, 209
See application file for complete search history.

(56) References Cited

U.S. PATENT DOCUMENTS

| | | | |
|---|---|---|---|
| 3,404,109 A | 10/1968 | Milgrom | |
| 3,427,256 A | 2/1969 | Milgrom | |
| 3,427,334 A | 2/1969 | Belner | |
| 3,427,335 A | 2/1969 | Herold | |
| 3,538,043 A | 11/1970 | Herold | |
| 3,829,505 A | 8/1974 | Herold | |
| 3,941,849 A | 3/1976 | Herold | |
| 4,472,560 A | 9/1984 | Kuyper et al. | |
| 4,477,589 A | 10/1984 | Van Der Hulst et al. | |
| 4,954,561 A | 9/1990 | Gerkin et al. | |
| 5,032,671 A | 7/1991 | Harper | |
| 5,145,883 A | 9/1992 | Saito et al. | |
| 5,158,922 A | 10/1992 | Hinney et al. | |
| 5,470,813 A | 11/1995 | Le-Khac | |
| 5,482,908 A | 1/1996 | Le-Khac | |
| 5,545,601 A | 8/1996 | Le-Khac | |
| 5,563,221 A | 10/1996 | Pazos | |
| 5,605,939 A | 2/1997 | Hager | |
| 5,689,012 A | 11/1997 | Pazos et al. | |
| 5,795,952 A * | 8/1998 | Greco ............................ | 528/196 |
| 2005/0222361 A1* | 10/2005 | Zaschke et al. .................. | 528/44 |
| 2006/0167125 A1* | 7/2006 | Bauer et al. .................... | 521/172 |
| 2006/0229375 A1* | 10/2006 | Hsiao et al. .................... | 521/172 |
| 2007/0088146 A1 | 4/2007 | Nakamura et al. | |
| 2007/0265367 A1 | 11/2007 | Le-Khac et al. | |
| 2008/0021154 A1 | 1/2008 | Haider et al. | |
| 2010/0204353 A1* | 8/2010 | Casati ............................ | 521/137 |

FOREIGN PATENT DOCUMENTS

| | | |
|---|---|---|
| DE | 203 734 | 11/1983 |
| DE | 203 735 | 11/1983 |
| DE | 10 2004 047 406 A1 | 3/2006 |
| DE | 10 2008 000 243 A1 | 8/2009 |
| EP | 0 259 722 B1 | 3/1993 |
| EP | 0 700 949 A2 | 3/1996 |
| EP | 0 743 093 A1 | 11/1996 |
| EP | 0 761 708 A2 | 3/1997 |
| EP | 0 879 259 B1 | 7/2001 |
| EP | 1 112 243 B1 | 3/2004 |
| EP | 1 022 300 B1 | 9/2004 |
| EP | 1 471 086 A2 | 10/2004 |
| EP | 1 712 576 A1 | 10/2006 |
| EP | 1 790 678 A1 | 5/2007 |
| EP | 1 537 159 B1 | 9/2007 |
| EP | 1 842 866 A1 | 10/2007 |
| EP | 1 624 004 B1 | 8/2008 |
| EP | 1 632 513 B1 | 2/2009 |
| JP | 4-145123 | 5/1992 |
| JP | 5-163342 | 6/1993 |

(Continued)

OTHER PUBLICATIONS

U.S. Appl. No. 13/551,936, filed Jul. 18, 2012, Chilekar, et al.

(Continued)

*Primary Examiner* — John Cooney

(74) *Attorney, Agent, or Firm* — Oblon, McClelland, Maier & Neustadt, L.L.P.

(57) ABSTRACT

The present invention relates to a process for preparing polyether polyols, in which at least one hydroxyl-comprising fatty acid ester and/or at least one hydroxyl-modified fatty acid ester is reacted with the aid of a double metal cyanide catalyst in at least two process sections with in each case a mixture of ethylene oxide and at least one further alkylene oxide different from ethylene oxide.

12 Claims, No Drawings

(56) References Cited

FOREIGN PATENT DOCUMENTS

| WO | WO 97/27236 | 7/1997 |
|---|---|---|
| WO | WO 97/29146 | 8/1997 |
| WO | WO 97/40086 | 10/1997 |
| WO | WO 98/03571 | 1/1998 |
| WO | WO 98/16310 | 4/1998 |
| WO | WO 98/52689 | 11/1998 |
| WO | WO 99/31160 | 6/1999 |
| WO | WO 00/47649 | 8/2000 |
| WO | WO 00/73364 A1 | 12/2000 |
| WO | WO 02/28937 A2 | 4/2002 |
| WO | WO 03/078496 A1 | 9/2003 |
| WO | WO 2004/096744 A2 | 11/2004 |
| WO | WO 2006/047436 A1 | 5/2006 |
| WO | WO 2007/019051 A1 | 2/2007 |
| WO | WO 2007/020879 A1 | 2/2007 |
| WO | WO 2008/073729 A2 | 6/2008 |
| WO | WO 2009/138379 A2 | 11/2009 |
| WO | WO 2009/155427 A2 | 12/2009 |

OTHER PUBLICATIONS

U.S. Appl. No. 13/321,323, filed Nov. 21, 2011, Eling, et al.
U.S. Appl. No. 13/813,300, filed Jan. 30, 2013, Loeffler, et al.

* cited by examiner

POLYETHER POLYOLS, PROCESS FOR PREPARING POLYETHER POLYOLS AND THEIR USE FOR PRODUCING POLYURETHANES

The present invention relates to novel polyetherols, especially biobased polyetherols, and a process for preparing the novel polyetherols and their use for producing polyurethane materials, especially slabstock and molded flexible polyurethane foams.

In the present disclosure, the terms "biobased compound/biobased raw material", "renewable compound/renewable raw material", "natural compound/natural raw material" are used synonymously and all refer to compounds which are not produced from fossil raw materials such as petroleum, natural gas or coal, in contrast to the compounds of petrochemistry which are ultimately derived from natural gas or petroleum as starting materials.

The expression "fat-based compound/fat-based raw material" refers to a specific class of biobased compounds and describes compounds which are derived from fatty acids, in particular fatty acid esters. Here, the term "fatty acid esters" refers to monoesters, diesters or triesters of fatty acids; the last-named triesters of fatty acids are also referred to as triglycerides. Triglycerides are main constituents of natural fats or oils, for example castor oil or soybean oil.

The term "polyetherols" (polyether polyols) also comprises, for the purposes of the present invention, polyols which comprise both ether units and ester units.

polyetherols based on renewable raw materials can be prepared, for example, by ring-opening polymerization of alkylene oxides using biobased starter molecules. As biobased starter molecules, it is possible to use not only sorbitol, sugar or glycerol but also hydroxyl-comprising fatty acid esters and/or hydroxyl-modified fatty acid esters, for example fats or oils comprising hydroxy groups and/or hydroxy-modified fat derivatives, e.g. fat-based dimer diols. The class of fats and fat derivatives comprising hydroxy groups is already being used for producing polyurethanes by reaction with isocyanates. Examples which may be mentioned in this context are castor oil and Lesquerella oil, which both naturally have hydroxy groups and can thus be used directly in polyurethane formulations. In the case of other natural oils, for example soybean oil, sunflower oil, rapeseed oil or palm oil, hydroxy groups have to be introduced by means of chemical reactions to enable them to be used in polyurethane formulations or for reaction with alkylene oxides since they are generally triglycerides of saturated and unsaturated fatty acids and thus do not naturally comprise any hydroxy groups.

Hydroxyl-modification, i.e. the introduction of hydroxy groups, is generally carried out in the prevailing prior art by derivatization reactions or by modification of the double bonds of unsaturated fatty acid esters. According WO08073729 A2 or WO04096744 A2, this can be effected, for example, by hydroformylation of the double bonds with subsequent hydrogenation of the aldehyde. In addition, a person skilled in the art will know that the double bonds of natural oils can be epoxidized by reaction with peroxocarboxylic acids. The epoxidized fats which can be obtained in this way can be reacted with alcohols, water or, according to WO2007019051A1, also with carboxylic acids to form hydroxy groups. The alkoxylation of the hydroxy fats which can be obtained by this route and reaction to form polyurethane materials is described in EP 0 259 722 B1. It is also possible to introduce hydroxy groups by ozonolysis or by direct oxidation using oxygen. A further possibility for introducing hydroxy functions into fatty acid esters has been described in Adv. Synth. Catal. 2007, 349, 1604. The double bonds of the natural fats can in this way be converted firstly into carbonyl groups by reaction with dinitrogen monoxide. The carbonyl groups can subsequently be reduced to secondary hydroxy groups in the presence of hydrogen or hydrogen-donating reagents such as lithium aluminum hydride.

As mentioned above, the fats comprising hydroxy groups can be extended by polyether chains by catalytic reactions with alkylene oxides. This process step makes it possible to set a wide variety of hydroxyl numbers. In addition, alkoxylation also allows partial replacement of petrochemical polyetherols by biobased polyetherols, without adverse effects in respect of the mechanical properties, for example in flexible polyurethane (PU) foams, or in respect of the processability of the polyetherols in the formulations having to be accepted.

Since the above-described hydroxy-comprising fats and fat derivatives comprise ester groups which are sensitive toward basic conditions, the classical alkali metal hydroxide-catalyzed addition reaction of alkylene oxides cannot be employed for these biobased raw materials since the starter molecules will otherwise be decomposed by hydrolysis reactions. This would inevitably lead to poor mechanical properties in polyurethane applications and also has adverse effects on the processability of the polyols in PU formulations. Instead, recourse is made to the DMC-catalyzed addition reaction of alkylene oxides for this process step, since DMC catalysts (DMC=double metal cyanide) allow alkoxylation of the hydroxy groups without degradation of the ester units in the starter molecules. The preparation of fat-based alkylene oxide addition products by means of DMC catalysts is described, for example, in EP 1 112 243 B1 or in JP 5 163 342 A1 and in WO 06047436 A1. The use of castor oil alkoxylates in flexible polyurethane foams is described by document EP 1 537 159 B1.

In the production of highly elastic flexible foam, also known as HR (high resilience) foam, use is generally made of trifunctional polyols having a relatively high molecular weight in a typical molecular weight range of 4500-7500 g/mol. Such polyols usually comprise glycerol or trimethylolpropane as starter molecule onto which blocks of propylene oxide and ethylene oxide are added. The outer poly (ethylene oxide) block generally makes up 13-23% by weight of the total molecular weight. The addition reaction of ethylene oxide gives polyols having a primary hydroxyl group content in the range from 80 to 90%. Owing to this high primary hydroxyl group content, such polyols are also referred to as reactive polyols. These HR or reactive polyols are used both in slabstock foams and in molded foams. HR foam is defined in the ASTM method D3770-91; however, a broader range of foams is recognized as HR foam in industry.

However, a person skilled in the art will know that reactive polyetherols which have to have a high proportion of terminal primary hydroxy groups cannot be obtained by means of the DMC-catalyzed addition reaction. Reactive polyetherols are, however, required in those polyurethane production processes in which rapid reaction of the hydroxy groups with the isocyanates is important. This is the case particularly when molded polyurethane components such molded flexible polyurethane foams or polyurethane shoe soles are to be produced. Here, the processor will require very short demolding times so that plant usage is optimal and a large number of polyurethane components can be produced in a given time. However, reactive polyetherols have hitherto been obtainable only via the classical alkali metal-catalyzed alkoxylation, which makes the use of base-sensitive biobased starter molecules impossible because of the abovementioned secondary reactions such as hydrolysis of the ester groups.

EP 1 842 866 A1 and EP 1 712 576 A1 describe processes for preparing polyetherols on the basis of natural oils and their use in polyurethane foams or polyurethane elastomers. This document also claims, inter alia, the process for producing products having a pure poly(ethylene oxide) end block.

However, a person skilled in the art will know that the use of pure ethylene oxide as end block in the DMC-catalyzed addition onto hydroxy-functional starter molecules leads to inhomogeneous and turbid products. This phenomenon has already been described in the teaching of U.S. Pat. No. 5,563,221 and can be explained by the DMC catalyst preferentially catalyzing the addition of ethylene oxide (EO) onto the primary hydroxy groups and not onto the secondary hydroxy groups. This leads to some polyether chains having very long poly(ethylene oxide) end blocks, while other polyether chains do not have any poly(ethylene oxide) end blocks. Since the molecules having the long poly(ethylene oxide) chains are incompatible with the polyether core block which usually comprises a hydrophobic poly(propylene oxide (PO)) block or a poly(propylene oxide)-poly(ethylene oxide) mixed block having a high proportion of poly(propylene oxide), this leads to phase separations which cause undesirable visible turbidity of the products. The turbid products are also not phase stable in the long term; a two-phase mixture of poly (ethylene oxide)-rich phases and phases which are low in poly(ethylene oxide) is formed after a prolonged period. The abovementioned higher reactivity of the primary hydroxy groups compared to the secondary hydroxy groups of the polyether core block also leads to the products having only a low proportion of terminal primary hydroxy groups, which is undesirable for use for the production of molded polyurethane foam.

A further disadvantage of such polyols is the narrow processing window. This means that, depending on the polyol architecture, for example in polyurethane (PU) production, foams which are either too unstable or too closed-celled are obtained. In the first case, foam collapse can occur in extreme cases or a foam which is coarse-celled with significantly higher densities than expected is obtained. In the second case, the foams in the extreme case display shrinkage or a significantly reduced air permeability. To alleviate this deficiency, for example as described in DE102004047406, the molecular weight and the poly(ethylene oxide) content of the polyol are selected so that foams having good properties are obtained. In EP97/00306, the length of the first addition block comprising poly(propylene oxide) was restricted to 35%.

EP 1 790 678 A1 describes a process for the in situ preparation of polyetherols based on vegetable oil by epoxidation/ring-opening of natural oils such as soybean oil with subsequent DMC-catalyzed alkoxylation. The document states that, in one embodiment, pure ethylene oxide or mixtures of propylene oxide and ethylene oxide having a high proportion of ethylene oxide can preferably be introduced as end block so that the polyether chains bound to the modified triglycerides and any costarter compounds added have from 40 to 100% primary OH end groups. However, a person skilled in the art will know that to obtain a proportion of more than 40% of primary terminal hydroxy groups, the ethylene oxide to propylene oxide ratio in the end block would have to be so high that turbid and inhomogeneous products would inevitably result.

As mentioned above, the document EP 1 537 159 B1 describes the use of DMC-catalyzed alkylene oxide addition products onto castor oil for the production of polyurethane foams. It is mentioned there that the polyetherols preferably have a pure poly(propylene oxide) end block. These products can be readily used in slabstock flexible polyurethane foams.

However, owing to the low reactivity mentioned and the relatively low molecular weight, they can be used to only a very restricted extent in molded HR flexible polyurethane foams or in molded polyurethane foams, e.g. shoe soles. Although it is mentioned in this document that polyetherols having a high content of primary hydroxy groups due to a pure ethylene oxide end block are usually used for molded flexible foams, no details are given regarding the process by means of which such products can be obtained.

EP 1 632 513 B1, EP 1 022 300 B1 and U.S. Pat. No. 5,605,939 A1 describe processes for the preparation or the use of reactive polyetherols which have a DMC-catalyzed poly(alkylene oxide) core block and an alkali metal-catalyzed poly(ethylene oxide) end block. However, the process for preparing these products cannot be employed in the case of hydroxy-functionalized fatty acid esters as starter component since this would, as mentioned above, decompose under the basic conditions of alkali metal catalysis.

In summary, it can be said that phase-stable biobased polyetherols have hitherto been obtainable by means of the DMC technology only when the products have a pure poly(propylene oxide) end block or a poly(propylene oxide)-poly(ethylene oxide) mixed block having a high proportion of poly (propylene oxide). However, as mentioned above, these products have limited suitability for the production of molded polyurethane foams because of the terminal secondary hydroxy groups.

Biobased reactive, clear and phase-stable polyetherols are nevertheless of commercial interest because of the sustainability discussion.

In addition, the abovementioned properties are also desirable in the case of polyetherols based on petrochemical raw materials.

Furthermore, it is desirable for polyetherols, in particular biobased polyetherols, to be readily processable in polyurethane (PU) formulations and to impart good mechanical properties to the PU products. In particular, the polyetherols should be able to be used readily for the production of highly elastic molded and slabstock flexible polyurethane foams.

It was therefore an object of the present invention to develop a process which makes it possible to obtain reactive, phase-stable and clear polyetherols having advantageous processing properties and mechanical properties in PU formulations, with preparation from biobased raw materials being a particular focus.

The object of the present invention has been able to be solved by the DMC-catalyzed addition of alkylene oxides onto the biobased starter molecules being carried out in at least two process sections in at least two different poly(alkylene oxide) blocks, with the addition reaction in each case having to be carried out using ethylene oxide.

The present invention accordingly provides a process for preparing polyether polyols, wherein at least one hydroxyl-comprising fatty acid ester and/or at least one hydroxyl-modified fatty acid ester is reacted with the aid of a double metal cyanide catalyst in at least two process sections with in each case a mixture of ethylene oxide and at least one further alkylene oxide different from ethylene oxide.

For the purposes of the present invention, a "process section" is in each case one of at least two different phases of the process of the invention which differ from one another in terms of the respective composition of the mixture of ethylene oxide and at least one further alkylene oxide different from ethylene oxide fed in, with the respective composition of a mixture remaining constant for a period of at least one minute, preferably for a period of at least 30 minutes, in a process section. Here, variations in the mass ratio of the compounds comprised in the respective mixture of up to 1% are still considered to be constant.

In this context, the term "composition" refers both to the compounds comprised in the respective mixture and also the mass ratios of these to one another.

This means, for example, that in a first process section a mixture of ethylene oxide and propylene oxide having a constant mass ratio is introduced for one hour. As soon as, after a pause in addition for a further 30 minutes, a mixture of ethylene oxide and 1,2-butylene oxide having a constant mass ratio is introduced, this represents a new process section.

Likewise, it is possible, for example, to introduce a mixture of ethylene oxide and propylene oxide in a constant mass ratio of 40:60 for two hours in a first process section. When this mass ratio is, for example after a pause in addition or a slow continuous modification ("ramp"), varied and a mixture of ethylene oxide and propylene oxide in a constant mass ratio of 50:50 is then introduced over a period of one hour, this likewise represents a new process section.

The composition of the respective mixture introduced in a process section does not have to be different from all other compositions of the respective mixtures introduced in all individual process sections; it suffices for the composition of the mixture introduced in a specific process section to differ from the respective compositions of the mixtures introduced in the preceding process section and any subsequent process section.

The change from one process section to the next can, for example, be carried out by firstly introducing a particular first mixture having a constant composition over a particular period of time, then pausing the introduction and subsequently introducing a second mixture having a constant composition over a particular period of time, with the second mixture differing in terms of its composition from the first mixture. As an alternative, the change from one process section to the next can also be, for example, such that a particular first mixture having a constant composition is introduced over a particular period of time, the composition of this mixture is then changed continuously, i.e. via a ramp, and a second mixture having a constant composition is then introduced over a particular period of time, with the second mixture differing in terms of its composition from the first mixture.

In a preferred embodiment, the process of the invention comprises precisely two process sections.

The constituents of the respective mixture of ethylene oxide and at least one further alkylene oxide different from ethylene oxide can be metered separately into the reaction vessel via separate inlets, in which case the respective mixture is then formed in-situ, or can be combined to form a mixture, for example in an upstream further vessel, before entry into the reaction vessel.

Preference is given to combining the mixture of the alkylene oxides before entry into the reaction vessel.

In each of the individual process sections, ethylene oxide and at least one further alkylene oxide different from ethylene oxide are preferably introduced simultaneously, as a result of which a mixture of ethylene oxide and at least one further alkylene oxide different from ethylene oxide having a constant composition is in each case present in the reactor.

In a preferred embodiment of the process of the invention, the introduction of the ethylene oxide and the introduction of the at least one further alkylene oxide different from ethylene oxide are switched off simultaneously at the end of the last process section (addition of the "cap" or end block). In this context, "simultaneously" means that the respective additions of the various alkylene oxides, which can, as described above, be combined directly in-situ in the reaction vessel or be combined to form a mixture before entry into the reaction vessel, are switched off within a time of less than 20 seconds, preferably less than 10 seconds, particularly preferably less than 5 seconds, from one another.

This ensures that the composition of the mixture introduced in the last process section remains constant until the end of the addition. This is helpful in avoiding the abovementioned disadvantages such as formation of long poly(ethylene oxide) end blocks.

It has surprisingly been found that the use of alkylene oxide/ethylene oxide mixtures for the first mixed block or blocks (core) which is/are produced in the first process section or sections is advantageous for the clarity and phase stability of the products. The use of alkylene oxide/ethylene oxide mixed blocks in the terminal end block produced in the last process section is advantageous for the reactivity of the products. Furthermore, the polyetherols of the invention can be readily processed in polyurethane formulations, which is assumed to be attributable to the proportion of EO in the core block, and in PU applications lead to open-celled foams.

Thus, the products of the invention differ structurally from the classical molded flexible foam polyetherols in that they comprise mainly or exclusively a) fat-based starters, b) they have no pure poly(ethylene oxide) end block and c) they have no pure poly(propylene oxide) core block.

As DMC (double metal cyanide) catalysts, preference is given to using Co—Zn, Fe—Zn, and/or Ni—Zn-based double metal cyanide catalysts; particular preference is given to using zinc hexacyanocobaltate catalysts as have been described, for example, in U.S. Pat. No. 3,404,109, U.S. Pat. No. 3,427,256, U.S. Pat. No. 3,427,334, U.S. Pat. No. 3,427,335, U.S. Pat. No. 3,829,505, U.S. Pat. No. 3,941,849, U.S. Pat. No. 4,472,560, U.S. Pat. No. 4,477,589, U.S. Pat. No. 5,158,922, U.S. Pat. No. 5,470,813, U.S. Pat. No. 5,482,908, U.S. Pat. No. 5,545,601, EP 0 700 949, EP 0 743 093, EP 0 761 708; WO 97/40086, WO 98/16310, WO 00/47649 and JP 4 145 123. The catalyst concentration is usually in the range from 5 to 1000 ppm, preferably from 20 to 250 ppm, particularly preferably from 50 to 150 ppm, based on the total mass of the final product to be prepared.

The DMC catalyst can be initially placed in the reaction vessel either directly as a solid or as a suspension in a polyetherol together with the biobased starter. As suspension polyetherols, use is generally made of alkylene oxide addition products of bifunctional, trifunctional, tetrafunctional or pentafunctional alcohols such as monopropylene glycol, dipropylene glycol, monoethylene glycol, diethylene glycol, 1,4-butanediol, glycerol, trimethylolpropane or pentaerythritol according to the prior art. These suspension polyetherols usually have a molecular weight in the range from 300 to 5000 g/mol, preferably from 300 to 1000 g/mol, and are generally obtained by the alkali metal-catalyzed addition reaction of alkylene oxides.

The alkylene oxides different from ethylene oxide which are used in the respective mixture in the process of the invention are preferably selected from the group consisting of propylene oxide, 1,2-butylene oxide, 2,3-butylene oxide, isobutylene oxide, 1,2-pentene oxide, styrene oxide, epichlorohydrin, cyclohexene oxide, and higher alkylene oxides such as $C_5$-$C_{30}$-α-alkylene oxides.

In a preferred embodiment, a mixture of ethylene oxide and precisely one further alkylene oxide different from ethylene oxide is used in at least one process section. In a particularly preferred embodiment, a mixture of ethylene oxide and precisely one further alkylene oxide different from ethylene oxide is used in all process sections.

In a preferred embodiment, at least one further alkylene oxide different from ethylene oxide in the respective mixture in at least one process section is selected from the group consisting of propylene oxide, 1,2-butylene oxide, 2,3-butylene oxide.

In a likewise preferred embodiment, all further alkylene oxides different from ethylene oxide in the respective mixture in at least one process section are selected from the group consisting of propylene oxide, 1,2-butylene oxide, 2,3-butylene oxide.

In a particularly preferred embodiment, at least one further alkylene oxide different from ethylene oxide in the respective mixture is selected from the group consisting of propylene oxide, 1,2-butylene oxide, 2,3-butylene oxide in all process sections. In a likewise particularly preferred embodiment, all further alkylene oxides different from ethylene oxide in the respective mixture are selected from the group consisting of propylene oxide, 1,2-butylene oxide, 2,3-butylene oxide in all process sections.

In a further preferred embodiment, at least one further alkylene oxide different from ethylene oxide in the respective mixture in at least one process section is propylene oxide.

In a further preferred embodiment, at least one further alkylene oxide different from ethylene oxide in the respective mixture is propylene oxide in all process sections. In a particularly preferred embodiment, a mixture consisting of ethylene oxide and propylene oxide is used in at least one process section.

In a further particularly preferred embodiment, a mixture consisting of ethylene oxide and propylene oxide is used in all process sections.

In a further particularly preferred embodiment, the process of the invention comprises precisely two process sections, with a mixture consisting of ethylene oxide and propylene oxide being used in both process sections.

In a preferred embodiment of the process of the invention for preparing polyether polyols, the mixture of ethylene oxide and at least one further alkylene oxide different from ethylene oxide in the process sections preceding the last process section in each case comprises ethylene oxide in a mass ratio to the total mass of all further alkylene oxides different from ethylene oxide present in the mixture in the range from 35:65 to 1:99, preferably from 30:70 to 5:95.

In a further preferred embodiment of the process of the invention for preparing polyether polyols, the mixture of ethylene oxide and at least one further alkylene oxide different from ethylene oxide in the last process section comprises ethylene oxide in a proportion by mass of the total mass of all further alkylene oxides different from ethylene oxide which are comprised in the mixture in the range from 35:65 to 75:25, preferably from 40:60 to 70:30.

In a particularly preferred embodiment of the process of the invention for preparing polyether polyols, the mixture of ethylene oxide and at least one further alkylene oxide different from ethylene oxide in the process sections preceding the last process section in each case comprises ethylene oxide in a proportion by mass of the total mass of all further alkylene oxides different from ethylene oxide which are comprised in the mixture in the range from 35:65 to 1:99, preferably from 30:70 to 5:95, and in the last process section comprises ethylene oxide in a proportion by mass of the total mass of all further alkylene oxides different from ethylene oxide comprised in the mixture in the range from 35:65 to 75:25, preferably from 40:60 to 70:30.

In a preferred embodiment, the proportion by mass of the total ethylene oxide units comprised in the polyetherol which can be prepared according to the invention is from 10 to 35% by weight, preferably from 15 to 30% by weight, based on all alkylene oxide units comprised.

In the process of the invention, a poly(alkylene oxide) block is thus firstly produced in the first process section, with the first poly(alkylene oxide) block comprising a certain proportion of ethylene oxide (EO) units and at least one further alkylene oxide (AO) unit. In a second process section, a second poly(alkylene oxide) block is then produced and added onto the first poly(alkylene oxide) block, with the second poly(alkylene oxide) block likewise comprising EO units and at least one further AO unit but the compositions of the blocks, as defined above, being different from one another.

The alkylene oxide units comprised in addition to the EO units in the respective poly(alkylene oxide) blocks do not necessarily have to be identical. Thus, for example, propylene oxide (PO) units can be comprised in addition to EO units in the first poly(alkylene oxide) block, while propylene oxide units and 1,2-butylene oxide units can be comprised in addition to EO units in the second poly(alkylene oxide) block.

If desired, a further poly(alkylene oxide) block or a plurality of further poly(alkylene oxide) blocks can be added on in one or more further process section(s) after the production and addition of the second poly(alkylene oxide) block, with the composition of the respective block to be added on, as defined above, once again differing from the composition of the respective preceding block.

According to the invention, use is made of at least a proportion of biobased starter molecules, in particular at least one hydroxyl-comprising fatty acid ester and/or at least one hydroxyl-modified fatty acid ester.

Here, the proportion of the biobased raw material in the polyetherol which can be prepared according to the invention is preferably in the range from 10% by weight to 40% by weight, particularly preferably from 15% by weight to 35% by weight.

In one embodiment, precisely one hydroxyl-comprising fatty acid ester or precisely one hydroxyl-modified fatty acid ester is used.

In a further embodiment, precisely one hydroxyl-comprising fatty acid ester and precisely one hydroxyl-modified fatty acid ester is used in each case.

In a preferred embodiment, at least one hydroxyl-comprising fatty acid ester and/or at least one hydroxyl-modified fatty acid ester is selected from the group consisting of hydroxyl-comprising fats, hydroxyl-comprising oils, hydroxyl-modified fats, hydroxyl-modified oils.

In a further preferred embodiment, all hydroxyl-comprising fatty acid esters and/or hydroxyl-modified fatty acid esters are selected from the group consisting of hydroxyl-comprising fats, hydroxyl-comprising oils, hydroxyl-modified fats, hydroxyl-modified oils.

In one embodiment, hydroxyl-modified cottonseed oil, grapeseed oil, black cumin oil, pumpkin kernel oil, borage seed oil, soybean oil, wheat germ oil, rapeseed oil, maize oil, linseed oil, palm oil, palm kernel oil, coconut oil, sunflower oil, peanut oil, apricot kernel oil, pistachio nut oil, almond oil, olive oil, macadamia nut oil, avocado oil, sea buckthorn oil, sesame oil, hemp oil, hazelnut oil, walnut oil, evening primrose oil, wild rose oil, hemp oil, safflower oil, herring oil, sardine oil and/or tallow are used. Fat-based dimers diols (Sovermol® 908 from Cognis GmbH or Pripol® 2033 from Croda GmbH) can also be used.

Particular preference is given to using castor oil, partially dehydrated castor oil (Sovermol® 1005 from Cognis GmbH), hydroxysoybean oil, hydroxysunflower oil, hydroxyrapeseed oil and/or hydroxypalm oil. The introduction of hydroxy groups into the natural oils can be carried out by the generally known and above-described processes, for example by hydroformylation/hydrogenation or epoxidation/ring-opening or ozonolysis, direct oxidation, nitrous oxide oxidation/reduction. Very particular preference is given to using castor oil.

The addition reaction of the alkylene oxides in the respective process sections is usually carried out at temperatures in the range from 60° C. to 180° C., preferably from 100 to 140° C., at pressures in the range from 0 to 20 bar, preferably from 0 to 10 bar. In a specific embodiment, the addition reaction of the various poly(alkylene oxide) mixed blocks is carried out at different temperatures in the respective process sections. The polyaddition can be carried out in bulk or in an inert organic solvent such as toluene and/or tetrahydrofuran. The amount of solvent is usually from 10% by weight to 30% by weight, based on the amount of the final product to be prepared.

The mixture of the biobased starter substance and the DMC catalyst can be pretreated by stripping before commencement of the reaction with alkylene oxides, as per the teaching of WO 98/52689.

In a further embodiment, one or more further starter alcohols (costarters), which can be identical to or different from the alcohol initially charged, can be introduced in addition to the alkylene oxides during the synthesis, in a manner analogous to the disclosure of DD 203734/735 and EP 879 259 B1. Such starter compounds preferably have functionalities of 2-8. Examples are propylene glycol, ethylene glycol, diethylene glycol, dipropylene glycol, 1,2-, 1,3-, 1,4-butanediol, hexanediol, pentanediol, 3-methyl-1,5-pentanediol, 1,12-dodecanediol, glycerol, trimethylolpropane, triethanolamine, pentaerythritol, sorbitol, sucrose, hydroquinone, catechols, resorcinol, bisphenol F, bisphenol A, 1,3,5-trihydroxybenzene, methylol-comprising condensates of formaldehyde and phenol or melamine or urea, and also Mannich bases.

Examples of monoamines or polyamines which may be added are ethylenediamine, 1,3-diaminopropane, 1,4-diaminobutane, hexamethylenediamine, ethanolamine, diethanolamine, diethylenetriamine, aniline, piperazine, the isomers of toluenediamine and the isomers of (diaminodiphenyl)methane. However, preference is given to adding costarters which are free of amino groups since these do not have an adverse effect on the DMC activity.

The costarters can also have been preextended by alkylene oxide addition in a preceding step, for example in order to liquefy them or to increase their compatibility with the reaction mixture.

Further suitable costarter compounds are polyesterols which are, according to the prevailing prior art, generally prepared by catalyzed condensation of organic dicarboxylic acids such as succinic acid, glutaric acid, adipic acid, suberic acid, azelaic acid, sebacic acid, decanedicarboxylic acid, dodecanedicarboxylic acid, maleic acid, fumaric acid, phthalic acid, isophthalic acid or terephthalic acid or mixtures thereof with polyhydric alcohols such as ethanediol, diethylene glycol, 1,2- or 1,3-propanediol, dipropylene glycol, methyl-1,3-propanediol, 1,4-butanediol, 1,5-pentanediol, 3-methyl-1,5-pentanediol, 1,6-hexanediol, neopentyl glycol, 1,10-decanediol, 1,12-dodecanediol, glycerol, trimethylolpropane, pentaerythritol or mixtures thereof at temperatures of from 150° C. to 300° C., preferably in the range from 180 to 230° C., and under reduced pressure. Preference is given to using dihydric alcohols for this purpose.

In a particular embodiment, further costarters can be initially placed in the reactor. However, the starter or the starter mixture or parts thereof can also be fed continuously into the reactor during the reaction together with the alkylene oxide(s). Here, an alkylene oxide addition product is usually initially placed in the reactor. This can be, for example, an addition product derived from the abovementioned starter compounds, in particular starter alcohols, or the reaction product of the process of the invention.

In a further embodiment, the reaction product can be taken off continuously from the reactor, in a manner analogous to the teaching of WO-A 97/29146 and WO-A 98/03571 and U.S. Pat. No. 5,689,012, so that the entire production process can be carried out entirely continuously. The DMC catalyst can also be fed in continuously, in general as a suspension in a polyol.

The DMC-catalyzed addition reaction of the alkylene oxides can be carried out in a manner analogous to the teaching of US 2007 0265367, U.S. Pat. No. 5,145,883, U.S. Pat. No. 3,538,043, U.S. Pat. No. 5,032,671, US 2007 0088146, WO 2007 020879, US 2008 0021154 in the presence of further monomers such as cyclic anhydrides (e.g. phthalic anhydride, trimellitic anhydride, pyromellitic anhydride, tetrahydrophthalic anhydride, maleic anhydride, itaconic anhydride, succinic anhydride) and/or cyclic esters (e.g. lactones, especially ϵ-caprolactone, γ-butyrolactone, lactides) and/or carbon dioxide.

In one embodiment, at least one of these additional components can have been prepared from renewable raw materials, e.g. by fermentation processes. For example, succinic acid can be prepared from renewable raw materials by fermentation processes and can be converted into succinic anhydride in a further process step. These monomers can either be placed together with the starter compound in the reaction vessel or all or part of them can be introduced together with the alkylene oxides during the reaction.

After the addition reaction of the alkylene oxides is complete, the polyether alcohols is generally worked up by means of conventional methods by removing the unreacted alkylene oxides and also volatile constituents, usually by distillation, steam stripping or gas stripping and/or other methods of deodorization. If necessary, a filtration can also be carried out.

If appropriate, antiaging agents such as antioxidants can be added to the reaction products obtainable by the process of the invention.

Furthermore, for example, it is possible to add additives which further improve the phase stability of the polyol of the invention or mixtures thereof with other polyols and help avoid turbidity in the polyetherols. In general, these are components which are surface-active. There are many surface-active substances, for example surfactants and polyalkylene glycols produced by BASF SE under the trade names Lutensol®, Plurafac®, Pluronic®, Pluriol® and Emulan®, and also silicates and silicone-comprising surfactants. A further class of surfactants is described in DE102008000243.

Further examples which may be mentioned here are commercially available preparations based on silicon dioxide, e.g. ES-P 150 from Evonik, Essen, Germany, or nonionic and ionic surfactants and also water.

The invention further provides a polyether polyol which can be prepared by the process of the invention.

The fat-based polyetherols which can be prepared according to the invention generally have hydroxyl numbers in the range from 100 to 10 mg KOH/g, preferably in the range from 50 to 20 mg KOH/g.

The functionality of the biobased polyetherols which can be prepared according to the invention is generally in the range from 1.5 to 6, preferably from 2 to 4. The molecular weights are generally in the range from 1000 to 10 000 g/mol, preferably from 1500 to 7000 g/mol, particularly preferably from 2000 to 6000 g/mol.

The viscosity of the polyetherol products is generally in the range from 200 to 20 000 mPas, preferably from 400 to 6000 mPas.

The proportion of terminal primary hydroxy groups in the polyetherol products is generally in the range from 10 to 40%, preferably from 20 to 40%.

In a preferred embodiment of the process of the invention for preparing polyether polyols, castor oil is used as oil and zinc hexacyanocobaltate is used as double metal cyanide catalyst, where the process comprises two process sections and the mixture of at least two different alkylene oxides in both process sections in each case consists of ethylene oxide and propylene oxide, with the mixture of at least two different alkylene oxides in the first process section comprising ethylene oxide and propylene oxide in a mass ratio in the range from 10:90 to 20:80 and the mixture of ethylene oxide and at least one further alkylene oxide different from ethylene oxide in the second process section comprising ethylene oxide and propylene oxide in a mass ratio in the range from 50:50 to 70:30.

The present invention thus further provides a polyether polyol which can be prepared from castor oil, ethylene oxide and propylene oxide using a DMC catalyst and has an OH number in the range from 20 to 50 mg KOH/g, a viscosity of from 500 to 1500 mPas, an acid number of from 0.001 to 0.1 and a content of primary OH groups in the range from 20% to 40%.

The polyetherols of the invention can, inter alia, also be used for producing solid-filled polyetherols (also referred to as polymer polyetherols, polymer-filled polyetherols or graft polyetherols).

Solid-filled polyols are a specific type of polyol dispersions.

Polyol dispersions comprise a continuous phase (liquid) and a solid phase which is dispersed in the continuous phase. Here, the continuous phase comprises at least one polyol and optionally further components, for example additionally a polyisobutene. The solid phase comprises at least one filler; the fillers are preferably selected from among polymeric, organic or inorganic fillers and mixtures thereof.

In the case of polymer polyols, the fillers are selected from among polymeric fillers, in particular from among copolymers of styrene with acrylonitrile.

Graft polyols or polymer polyols are used as raw materials in the polyurethane (PU) industry in order to adjust the hardness and elasticity properties of flexible PU foams. They are generally polyetherols (continuous phase) filled with a copolymer of styrene and acrylonitrile (styrene-acrylonitrile polymer, SAN; as filler, solid phase). The process for preparing the polymer polyols comprises copolymerization of ethylenically unsaturated monomers with a macromer.

Such polyols have been known for a long time and are described, for example, in WO 03/78496. Foams produced using graft polyols usually have an increased hardness and an improved proportion of open cells.

The macromer performs the function of steric stabilization of the SAN particles formed and thus prevents agglomeration or flocculation of the SAN particles. Furthermore, the particle size can be set in a targeted manner via the amount of macromer used. Macromers used are usually polyfunctional polyetherols which have subsequently been provided with an unsaturated bond which can be polymerized with the comonomers by a free-radical mechanism.

Preference is given to at least one, particularly preferably all, of the fillers being selected from the group consisting of polystyrene, poly(styrene-co-acrylonitrile), polyacrylonitrile, polyacrylate, polymethacrylate, polyolefin, e.g. polypropylene, polyethylene, polyisobutylene, polybutadiene, polyester, polyamide, polyvinyl chloride, polyethylene terephthalate, polyethylene glycol, sulfur, phosphorus, silicate materials (e.g. silica nanoparticles), metal oxides, metal carbonates, inorganic salts, inorganic pigments, carbon (e.g. graphite, nanotubes, fibers), melamine, urea, cellulose (e.g. fibers, nanoparticles, crystalline cellulose).

The fillers can be mixed with one another and the total amount of the fillers, based on the total mixture, is preferably in the range from 1 to 70% by weight, particularly preferably from 5 to 60% by weight.

The distribution of the fillers can be monomodal, bimodal or multimodal.

In one embodiment, the particle size of at least one, preferably all, of the fillers is in each case 0.05 µm-500 µm, particularly preferably 0.1 µm-20 µm.

The present invention thus further provides a process for preparing solid-filled polyetherols, wherein a polyetherol which can be prepared by the process of the invention is reacted with at least one unsaturated monomer in the presence of a macromonomer.

The unsaturated monomers are preferably selected from the group consisting of styrene, α-methylstyrene and acrylonitrile.

The macromonomer is preferably, according to the teachings of WO 99031160 A1 and U.S. Pat. No. 4,954,561 B1, a reaction product of a polyfunctional polyether polyol having a functionality of 2-6, preferably 3-6, and an average molecular weight of 1000-50 000, preferably 5000-20 000, with an ethylenically unsaturated, free-radically polymerizable isocyanate, preferably 1,1-dimethyl-meta-isopropenylbenzyl isocyanate (TMI) or isocyanatoethyl methacrylate (IEM). As an alternative, the macromer can also be a reaction product of a polyfunctional polyetherol having a functionality of 2-6, preferably 3-6, and an average molecular weight of 1000-50 000, preferably 5000-20 000, with an unsaturated cyclic anhydride, preferably maleic anhydride, with subsequent reaction of the resulting intermediate with alkylene oxides. A further possibility is to use a macromer which, according to the teaching of EP 1 624 004 B1, can be prepared by reaction of a polyfunctional polyether polyol with a (meth)acrylate or (meth)acrylic acid.

Further solid-filled polyetherols which may be mentioned are polyisocyanate polyaddition polyols (PIPA polyols). The present invention thus also provides a process for preparing polyisocyanate polyaddition polyols (PIPA polyols), in which polyisocyanates, preferably tolylene diisocyanate (TDI), diphenylmethane diisocyanate (MDI) and/or polymethylenepolyphenylene polyisocyanates (crude MDI), are reacted with low molecular weight compounds which have a plurality of hydroxy, primary amino and/or secondary amino functions in the presence of compounds having at least two hydrogen atoms which are reactive toward isocyanates and have a molecular weight in the range from 500 to 10 000 g/mol and, if appropriate, catalysts. The compounds having at least two hydrogen atoms which are reactive toward isocyanates are preferably selected from the group consisting of polyether polyols which can be prepared according to the invention. The low molecular weight compounds are preferably selected from the group consisting of alkanolamines, in particular triethanolamine and/or diethanolamine in a manner analogous to the teachings of WO 00/73364 A1.

Polyols comprising dispersed polyureas, also referred to as polyurea dispersion polyols (PUD polyols), also come under the class of solid-filled polyether polyols and are thus provided by the present invention.

They are prepared using polyamines having primary and/or secondary amino groups which are reacted with monoisocyanates, diisocyanates and/or polyisocyanates to give polyurea dispersions. The base polyetherols used are usually bifunctional and/or higher-functional.

The base polyetherols are preferably selected from the group consisting of the polyether polyols which can be prepared according to the invention.

In a further embodiment of a solid-filled polyetherol, a dispersion of melamine in combination with at least one amine and also at least one organic and/or modified organic isocyanate in the polyol component is used as flame retardant. Here, the polyols are preferably selected from the group consisting of the polyether polyols which can be prepared according to the invention.

The process of the invention for preparing solid-filled polyetherols can also comprise steps of a melt emulsification process as described, for example, in WO 2009 138 379 A2 and WO 0 228 937 A2 and WO 09 155 427 A2.

The present invention further provides for the use of the polyether polyol which can be prepared by the process of the invention and/or the solid-filled polyetherol which can be prepared from the polyetherol which can be prepared by the process of the invention for producing polyurethanes and/or polyurethane formulations, in particular slabstock flexible polyurethane foam formulations, molded flexible polyurethane foam formulations, polyurethane shoe formulations or polyurethane elastomer formulations.

The polyetherols of the invention can be used in various polyurethane applications, especially when the polyurethanes are to have elastic properties, e.g. in the case of elastomers. The polyetherols of the invention can advantageously be used in the production of highly elastic slabstock or molded flexible polyurethane foams. In the production of highly elastic slabstock or molded flexible polyurethane foams, these polyols are reacted with MDI, TDI or MDI/TDI mixtures or with the corresponding isocyanate-terminated prepolymers. Here, the petrochemicals-based polyetherols which are customarily used can be replaced either partly or completely by the polyetherols of the invention.

Typical highly elastic flexible polyurethane foams have rebound resilience values in accordance with DIN EN ISO 8307 of 45-60%. (The polyurethanes book, Randall, Lee, eds. Wiley 2002, ISBN 0470850418). The required polyols are usually also referred to as HR or reactive polyols. Reactive polyols usually have a poly(ethylene oxide) end block of 13 to 20%, as a result of which the polyols have from 80 to 90% reactive primary hydroxy groups.

The polyols of the invention usually have similar EO contents but differ in the proportion of primary hydroxy groups (see above).

It has surprisingly been found that the polyols of the invention can be used as main polyol in the A component (polyol component) of a typical foam formulation for highly elastic flexible polyurethane foams. In this context, the term main polyol means that the polyol makes up more than 50% by weight of the total A component.

The present invention thus further provides a process for producing flexible polyurethane foams by catalyzed reaction of
a) polyisocyanates with
b) compounds having at least two hydrogen atoms which are reactive toward isocyanate groups,
c) blowing agents,
wherein the compounds b) having at least two hydrogen atoms which are reactive toward isocyanate groups comprise bi) 40-100 parts by weight of the polyetherol which can be prepared according to the invention,
bii) 0-60 parts by weight of a standard reactive polyol,
biii) 0-60 parts by weight of a graft polyol,
biv) 0-10 parts by weight of a cell-opener polyol,
bv) 0-10 parts by weight of a crosslinker.

The polyether alcohols bi) described can be reacted either alone or in admixture with other compounds having at least two hydrogen atoms which are reactive toward isocyanate groups to produce flexible polyurethane foams.

The production of the flexible polyurethane foams according to the invention is carried out by reacting the polyether alcohols with polyisocyanates. The reaction is usually carried out in the presence of blowing agents, catalysts and customary auxiliaries and/or additives. As regards the starting materials used, the following details may be provided.

As polyisocyanates a), use is made of all isocyanates having two or more isocyanate groups in the molecule. It is possible to use aliphatic isocyanates such as hexamethylene diisocyanate (HDI) or isophorone diisocyanate (IPDI) or preferably aromatic isocyanates such as tolylene diisocyanate (TDI), diphenylmethane diisocyanate (MDI) or mixtures of diphenylmethane diisocyanate and polymethylenepolyphenylene polyisocyanates (crude MDI). It is also possible to use isocyanates which have been modified by incorporation of urethane, uretdione, isocyanurate, allophanate, uretonimine and other groups, known as modified isocyanates.

As polyisocyanates a), preference is given to using TDI or MDI, its higher homologues and/or its reaction products with compounds having at least two hydrogen atoms which are reactive toward isocyanate groups.

For the production of slabstock flexible foams, particular preference is given to using TDI, while in the preferred production of molded foams, preference is given to using MDI and its higher homologues.

As compounds which have at least two groups which are reactive toward isocyanate groups and are, if necessary, used in admixture with the polyether alcohols of the invention, preference is given to using polyols. Among polyols, polyether polyols and polyester polyols have the greatest industrial importance. The polyether polyols used for producing polyurethanes are usually prepared by base-catalyzed addition of alkylene oxides, in particular ethylene oxide and/or propylene oxide, onto H-functional starter substances. Polyester polyols are usually prepared by esterification of polyfunctional carboxylic acids with polyfunctional alcohols. The polyols used preferably have a hydroxyl number in the range from 20 to 100 mg KOH/g and a functionality in the range from 2 to 4.

Particular preference is given to using standard reactive polyols (bii) having OH numbers of 20-40 mg KOH/g, in particular 25-35 mg KOH/g, and having an ethylene oxide cap of from 10 to 30% by weight, in particular from 13 to 23%, and an average functionality of 2-6, in particular 3-5. Here, the average functionality is the average functionality of the starters or of the starter mixture. As starters, it is possible to use, for example, glycerol, trimethylolpropane, pentaerythritol, sorbitol, sucrose, triethanolamine and ethylenediamine or mixtures thereof.

In a particular embodiment of the invention, component b) can comprise at least one graft polyol (biii). Such polyols are, as mentioned above, generally prepared by in-situ polymerization of ethylenically unsaturated monomers, in particular styrene and/or acrylonitrile, in carrier polyols, preferably polyether alcohols.

In a particular embodiment, the carrier polyol is (bi).

The polymerization is usually carried out in the presence of initiators, polymerization regulators and polyols having built-in ethylenically unsaturated bonds, frequently also referred to as macromers. Such polyols have been known for a long time and are described, for example, in WO 03/78496. Graft polyols preferred for the process of the invention have a hydroxyl number in the range from 10 to 50 mg KOH/g, a functionality of from 2 to 4 and a solids content of from 35 to 50% by weight. Foams produced using graft polyols usually have a higher hardness and an improved proportion of open cells.

Furthermore, it can be preferred to use other polyols such as ethylene oxide-propylene oxide polyether polyols having an ethylene oxide content of 50-80% and hydroxyl numbers of 28-55 mg KOH/g (cell-opener polyols, biv). Such polyols are used to improve processing and the mechanical properties.

The compounds having at least two groups which are reactive toward isocyanate groups also include chain extenders and/or crosslinkers which may be used concomitantly (bv). These are at least bifunctional amines and/or alcohols having molecular weights in the range from 60 to 400 g/mol.

As blowing agents (c), use is usually made of water, compounds which are inert toward the starting materials for the polyurethanes and are gaseous at the reaction temperature of the urethane reaction and/or physically acting blowing agents and also mixtures thereof. As physically acting blowing agents, use is usually made of hydrocarbons having from 2 to 6 carbon atoms, halogenated hydrocarbons having from 2 to 6 carbon atoms, ketones, acetals, ethers, inert gases such as carbon dioxide or noble gases.

As catalysts in the process of the invention for producing flexible PU foams, preference is given to using amine compounds and/or metal compounds, in particular heavy metal salts and/or metal-organic compounds. In particular, tertiary amines and/or organic metal compounds are used as catalysts. Possible organic metal compounds are, for example, tin compounds such as tin(II) salts of organic carboxylic acids, e.g. tin(II) acetate, tin(II) octoate, tin(II) ethylhexanoate and tin (II) laurate, and the dialkyltin(IV) salts of organic carboxylic acids, e.g. dibutyltin diacetate, dibutyltin dilaurate, dibutyltin maleate and dioctyltin diacetate. Organic amines customary for this purpose are, for example: triethylenediamine, bis(N, N-dimethylaminoethyl)ether, N,N-dimethylethanolamines, dimethyl-2-hydroxy(propyl)-1,3-propylenediamine, N,N-dimethylhexadecylamine, pentamethyldipropylenetriamine, triethylamine, 1,4-diazabicyclo[2.2.2]octane, tributylamine, dimethylbenzylamine, N,N,N',N'-tetramethylethylenediamine, N,N,N',N'-tetramethylbutanediamine, N,N,N',N'-tetramethylhexane-1,6-diamine, dimethylcyclohexylamine. The catalysts described can be used individually or in the form of mixtures.

In the process of the invention for producing flexible PU foams, it is possible to add further auxiliaries and/or additives such as mold release agents, flame retardants, dyes, fillers and/or reinforcing materials.

It is customary in industry to mix all starting materials with the exception of the polyisocyanates to form a polyol component (A component) and react this with the polyisocyanates to form the polyurethane.

The polyurethanes can be produced by the one-shot process or by the prepolymer process.

An overview of the starting materials for the production of polyurethanes and the processes employed for this purpose may be found, for example, in Kunststoffhandbuch, volume 7 "Polyurethane", Carl-Hanser-Verlag, Munich, Vienna, 1$^{st}$, edition 1966, 2$^{nd}$ edition 1983 and 3$^{rd}$ edition 1993.

The flexible polyurethane foams produced by the process of the invention have a high air permeability and good mechanical properties, in particular a high rebound resilience.

The polyetherols of the invention can, for example, likewise be used for the production of flexible foams by the hot molded foam process. Here, TDI (tolylene 2,4-diisocyanate) is usually utilized as isocyanate component. The polyols can likewise be used for producing polyurethane shoe soles. In this process, MDI (dimethylmethane isocyanate) is preferably used as isocyanate component. Furthermore, the polyols of the invention can be used for producing polyurethane coatings, polyurethane adhesives, polyurethane sealants or polyurethane elastomers ("Coatings, adhesives, sealants, elastomers", C.A.S.E.).

The polyols of the invention can be used not only in the A component (polyol component) of the polyurethane formulation but also in the B component (isocyanate component) in the form of prepolymers. Prepolymers based on the polyols of the invention can be used in all the abovementioned applications. Isocyanate-terminated prepolymers are prepared by reacting the polyetherols of the invention with an excess of the organic isocyanate or mixtures of various organic isocyanates.

The polyetherols of the invention, which are at least partly derived from biobased starting materials, can be used in combination with petrochemicals-based polyols such as the abovementioned polyethers and polyesters and also with polyacetals, polycarbonates, polyether esters, polyester carbonates, polythioethers, polyamides, polyesteramides, polysiloxanes, polybutadienes and/or polyacetones in polyurethane formulations.

The formulations, in particular the flexible polyurethane foam formulations, in which the polyetherols of the invention can be used generally comprise further additives such as foam stabilizers, catalysts, cell regulators, reaction retarders, flame retardants, plasticizers, pigments or fillers.

In a preferred embodiment, the formulation for a polyurethane which has been produced using the polyether polyols of the invention comprises at least 1% by weight, preferably more than 3%, particularly preferably more than 5%, of the renewable raw material used.

The invention is illustrated by the following examples which do not in any way restrict the scope of the invention.

EXAMPLES

General

Lupranol® 1100 is a bifunctional polyetherol having a hydroxyl number of 104 mg KOH/g from BASF Polyurethanes GmbH.

Synthesis of the Polyetherols of the Invention

Example A 144.6 kg of castor oil DAB 10 having a hydroxyl number of 162 mg KOH/g were placed in a pressure autoclave and admixed with 1.85 kg of a 5.4% strength suspension of a zinc hexacyanocobaltate catalyst in Lupranol® 1100. After the reaction mixture had been made inert three times by means of nitrogen, the autoclave was evacuated to 15 mbar at 130° C. for about 30 minutes in order to remove water. A mixture of 13 kg of propylene oxide and 2 kg of ethylene oxide were subsequently metered into the reaction mixture over a period of 10 minutes to activate the DMC catalyst. After activation of the catalyst, which could be recognized by an increase in temperature combined with a decrease in pressure in the reactor, a further 341 kg of propylene oxide and 47.9 kg of ethylene oxide were metered into the reaction mixture over a period of 90 minutes. After introduction of the monomer was complete and after a constant reactor pressure had been reached, the pressure of the reactor was increased to 3.5 bar by means of nitrogen and a mixture of 46.6 kg of propylene oxide and 69.8 kg of ethylene oxide was introduced as end block. This was again followed by an after-reaction phase until a constant reactor pressure had been reached. Volatile constituents were then distilled off under reduced pressure and the product was drained. This gave 650 kg of the desired biobased polyetherol in the form of a clear and phase-stable, slightly yellowish, viscous liquid.

| | | |
|---|---|---|
| Hydroxyl number: | 34.4 mg KOH/g | (DIN 53240) |
| Viscosity (at 25° C.): | 1035 mPas | (DIN 51550) |
| Acid number: | 0.012 mg KOH/g | (DIN EN ISO 2682) |
| Water content: | 0.027% | (DIN 51777) |
| Hazen color number: | 35 mg of Pt/t | (DIN 53409) |
| Primary hydroxy groups: | 26% | (determined by 1H-NMR spectroscopy) |
| pH: | 7.7 | |

Example B 144.6 kg of castor oil DAB 10 having a hydroxyl number of 162 mg KOH/g were placed in a pressure autoclave and admixed with 1.85 kg of a 5.4% strength suspension of a zinc hexacyanocobaltate catalyst in Lupranol® 1100. After the reaction mixture had been made inert three times by means of nitrogen, the autoclave was evacuated to 15 mbar at 130° C. for about 30 minutes in order to remove water. A mixture of 13 kg of propylene oxide and 2 kg of ethylene oxide were subsequently metered into the reaction mixture over a period of 10 minutes to activate the DMC catalyst. After activation of the catalyst, which could be recognized by an increase in temperature combined with a decrease in pressure in the reactor, a further 335 kg of propylene oxide and 37.9 kg of ethylene oxide were metered into the reaction mixture over a period of 90 minutes. After introduction of the monomer was complete and after a constant reactor pressure had been reached, the pressure of the reactor was increased to 3.5 bar by means of nitrogen and a mixture of 53.2 kg of propylene oxide and 79.8 kg of ethylene oxide was introduced as end block. This was again followed by an after-reaction phase until a constant reactor pressure had been reached. Volatile constituents were then distilled off under reduced pressure and the product was drained. This gave 650 kg of the desired biobased polyetherol in the form of a clear and phase-stable, slightly yellowish, viscous liquid.

| | | |
|---|---|---|
| Hydroxyl number: | 35.2 mg KOH/g | (DIN 53240) |
| Viscosity (at 25° C.): | 1000 mPas | (DIN 51550) |
| Acid number: | 0.010 mg KOH/g | (DIN EN ISO 2682) |
| Water content: | 0.017% | (DIN 51777) |
| Hazen color number: | 30 mg of Pt/t | (DIN 53409) |
| Primary hydroxy groups: | 25% | (determined by 1H-NMR spectroscopy) |
| pH: | 7.7 | |

Example C 144.6 kg of castor oil DAB having a hydroxyl number of 162 mg KOH/g were placed in a pressure autoclave and admixed with 1.85 kg of a 5.4% strength suspension of a zinc hexacyanocobaltate catalyst in Lupranol® 1100. After the reaction mixture had been made inert three times by means of nitrogen, the autoclave was evacuated to 15 mbar at 130° C. for about 30 minutes in order to remove water. A mixture of 13 kg of propylene oxide and 2 kg of ethylene oxide were subsequently metered into the reaction mixture over a period of 10 minutes to activate the DMC catalyst. After activation of the catalyst, which could be recognized by an increase in temperature combined with a decrease in pressure in the reactor, a further 350 kg of propylene oxide and 93.6 kg of ethylene oxide were metered into the reaction mixture over a period of 90 minutes. After introduction of the monomer was complete and after a constant reactor pressure had been reached, the pressure of the reactor was increased to 3.5 bar by means of nitrogen and a mixture of 25.0 kg of propylene oxide and 37.5 kg of ethylene oxide was introduced as end block. This was again followed by an after-reaction phase until a constant reactor pressure had been reached. Volatile constituents were then distilled off under reduced pressure and the product was drained. This gave 650 kg of the desired biobased polyetherol in the form of a clear and phase-stable, slightly yellowish, viscous liquid.

| | | |
|---|---|---|
| Hydroxyl number: | 35.8 mg KOH/g | (DIN 53240) |
| Viscosity (at 25° C.): | 958 mPas | (DIN 51550) |
| Acid number: | 0.012 mg KOH/g | (DIN EN ISO 2682) |
| Water content: | 0.015% | (DIN 51777) |
| Hazen color number: | 30 mg of Pt/t | (DIN 53409) |
| Primary hydroxy groups: | 26% | (determined by 1H-NMR spectroscopy) |
| pH: | 7.9 | |

Synthesis of the Comparative Examples

Comparative Example A 951 g of castor oil DAB 10 having a hydroxyl number of 162 mg KOH/g were placed in a pressure autoclave and admixed with 14.0 g of a 5.47% strength suspension of a zinc hexacyanocobaltate catalyst in Lupranol® 1100. After the reaction mixture had been made inert three times by means of nitrogen, the autoclave was evacuated to 15 mbar at 130° C. for about 30 minutes in order to remove water. A mixture of 85.2 g of propylene oxide and 11.4 g of ethylene oxide were subsequently metered into the reaction mixture over a period of 10 minutes to activate the DMC catalyst. After activation of the catalyst, which could be recognized by an increase in temperature combined with a decrease in pressure in the reactor, a further 2578.4 g of propylene oxide and 345.6 g of ethylene oxide were metered into the reaction mixture over a period of 90 minutes. After introduction of the monomer was complete and after a constant reactor pressure had been reached, the pressure of the reactor was increased to 3.5 bar by means of nitrogen and a mixture of 82.4 g of propylene oxide and 329.5 g of ethylene oxide was introduced as end block. This was again followed by an after-reaction phase until a constant reactor pressure had been reached. Volatile constituents were then distilled off under reduced pressure and the product was drained. This gave 4300 g of a turbid polyetherol which separated into two phases after a number of days.

| | | |
|---|---|---|
| Hydroxyl number: | 36.2 mg KOH/g | (DIN 53240) |
| Viscosity (at 25° C.): | 1040 mPas | (DIN 51550) |
| Primary hydroxy groups: | 32% | (determined by 1H-NMR spectroscopy) |

Comparative Example B 969.3 g of castor oil DAB 10 having a hydroxyl number of 162 mg KOH/g were placed in a pressure autoclave and admixed with 14.3 g of a 5.47% strength suspension of a zinc hexacyanocobaltate catalyst in Lupranol® 1100. After the reaction mixture had been made inert three times by means of nitrogen, the autoclave was evacuated to 15 mbar at 130° C. for about 30 minutes in order to remove water. 120 g of propylene oxide were subsequently metered into the reaction mixture over a period of 10 minutes to activate the DMC catalyst. After activation of the catalyst, which could be recognized by an increase in temperature combined with a decrease in pressure in the reactor, a further 1921.9 g of propylene oxide were metered in over a period of 90 minutes. After the metering was complete and after a constant reactor pressure had been reached, the pressure of the reactor was increased to 3.5 bar by means of nitrogen and a mixture of 583.4 g of propylene oxide and 875.1 g of ethylene oxide was introduced as end block. This was again followed by an after-reaction phase until a constant reactor pressure had been reached. Volatile constituents were then distilled off under reduced pressure and the product was drained. This gave 4400 g of a clear and phase-stable polyetherol.

| | | |
|---|---|---|
| Hydroxyl number: | 35.0 mg KOH/g | (DIN 53240) |
| Viscosity (at 25° C.): | 1003 mPas | (DIN 51550) |
| Acid number: | 0.07 mg KOH/g | (DIN EN ISO 2682) |
| Water content: | 0.02% | (DIN 51777) |
| Primary hydroxy groups: | 30% | (determined by 1H-NMR spectroscopy) |

Use Examples

The production of specimens for mechanical testing was carried out as described below. The starting materials used for producing the polymer materials of the examples are shown in Tables 1a-b.

TABLE 1a

Polyols

| Polyol | Structure | OH number | EO content | Description |
|---|---|---|---|---|
| Polyol 1 | GLY-PO-EO | 35 | 14 | Reactive polyol |
| Polyol 2 | GLY-EO-PO hectic | 42 | 75 | Cell-opener polyol |
| Polyol 3 | Polymer polyol, 45% solids content | 19 | 14 | Reactive polymer polyol for molded applications |

GLY = glycerol,
EO = ethylene oxide,
PO = propylene oxide,

TABLE 1b

Isocyanates and additives

| Trade name | Manufacturer | Description |
|---|---|---|
| Isocyanate 1 | BASF | MDI prepolymer |
| Isocyanate 2 | BASF | TDI 80/20 |
| Tegostab 8715LF | Goldschmidt | surfactant |
| Tegostab B 8616 | Goldschmidt | surfactant |
| Niax A-1 | Air Products | amine catalyst |
| Dabco 33 LV | Air products | amine catalyst |
| Kosmos 29 | Air products | tin catalyst |
| Ortegol 204 | Air products | surfactant |
| Diethanolamine | BASF | crosslinker |
| Dabco 2025 | Air products | amine catalyst |

MDI-based molded foam (manual test):

The polyol formulation (A component) was weighed out according to the formulation recipe on a laboratory balance at room temperature. The blend obtained was homogenized by means of a laboratory stirrer for 1 minute and then left to stand at room temperature for 30 minutes. As B component, use was made of a prepolymer prepared from a mixture of 2-ring MDI having a content of 40% by weight of 2,4'-MDI and 60% by weight of 4,4'-MDI and polymeric MDI (Lupranat M20W-BASF), prepolymerized with polyol 2. The ratio of 2-ring MDI, polymeric MDI and polyol 2 in the prepolymer was 55.0:40.0:5.0. The NCO content of the prepolymer was 30.7% (isocyanate 1). The prepolymer was prepared in a known manner (see, for example, EP1471086). Foaming was carried out at an isocyanate index of 90.

To carry out foaming, the amounts of A and B component required were weighed into a 2.5 l bucket. After stirring by means of a laboratory stirrer at 1500 rpm for 10 seconds, the mixture was poured into a 16 l mold (dimensions: 40×40×10 cm$^3$) which was at a temperature of 50° C. The amount of mixture introduced into the mold was 960 g; this corresponds to a foam density of 50 kg/m$^3$. After 6 minutes, the foam was taken from the mold and worked manually within 30 minutes.

TDI-Based Foam (Manual Test):

The polyol formulation (A component) was weighed out according to the formulation recipe but without tin catalyst on a laboratory balance at room temperature. The blend obtained was homogenized by means of a laboratory stirrer for 1 minute and then allowed to stand at room temperature for 30 minutes.

To carry out foaming, the amount of A component required was weighed into a 2.5 l bucket and the appropriate amount of tin catalyst was added. After addition of the catalyst, the mixture was stirred briefly. In the next step, the TDI was added. After stirring by means of a laboratory stirrer at 1500 rpm for 10 seconds, the mixture was poured into a 10.7 l cube (dimensions: 22×22×22 cm$^3$). Foaming was carried out at an isocyanate index of 100. The amount of mixture introduced was 650 g. After 30 minutes, the foam was taken from the mold and worked manually on the next day.

Mechanical Testing:

The foam density was determined in accordance with DIN EN ISO 845, the compressive strength was determined in accordance with DIN EN ISO 3386, the tensile strength and elongation at break were determined in accordance with DIN EN ISO1798, the compression set and the humid age compression set (HACS) were determined in accordance with DIN EN ISO 1856, the air permeability was determined in accordance with DIN EN ISO 7231, the rebound resilience was determined in accordance with DIN EN ISO 8307 and the tear propagation resistance was determined in accordance with DIN ISO 34-,B.

The wet compression set was determined by in-house test methods derived from ISO13362. The test specimens were sawn to I×b×$H_o$=50*50*25 mm³, compressed to 70% of the original height ($H_o$) to 7.5 mm ($H_a$) and stored at 50° C. and 95% relative atmospheric humidity for 22 hours. The compressive deformation ($H_t$) was measured after 30 minutes. The wet set was calculated according to equation (1):

$$\text{Wet set}=[(H_o-H_t)/(H_o-H_a)]*100\% \quad (1)$$

Use Examples I-III

|  |  | Example | | |
|---|---|---|---|---|
|  |  | I | II | III |
| Formulation |  |  |  |  |
| Polyol A | parts | 75 |  |  |
| Polyol B | parts |  | 75 |  |
| Polyol C | parts |  |  | 75 |
| Polyol 1 (L2095) | parts | 17.45 | 17.45 | 17.45 |
| Polyol 2 (L2048) | parts | 3.5 | 3.5 | 3.5 |
| Tegostab B 8715 LF | parts | 0.5 | 0.5 | 0.5 |
| Dabco 2025 | parts | 0.4 | 0.4 | 0.4 |
| Dabco 33 LV | parts | 0.45 | 0.45 | 0.45 |
| Tap water | parts | 2.6 | 2.6 | 2.6 |
| Isocyanate 1 | index = 90 |  |  |  |
| Reaction times |  |  |  |  |
| Cream time | s | 17 | 17 | 18 |
| Fiber time | s | 120 | 118 | 119 |
| Properties |  |  |  |  |
| Foam density | kg/m^3 | 49.3 | 49.4 | 48.8 |
| Compressive strength 25% | kPa | 2.1 | 2.0 | 2.1 |
| Compressive strength 40% | kPa | 2.7 | 2.6 | 2.7 |
| Compressive strength 65% | kPa | 5.7 | 5.6 | 5.7 |
| Hysteresis | % | 16.1 | 17.1 | 15.1 |
| Tensile strength | kPa | 70 | 65 | 70 |
| Elongation at break | % | 98 | 92 | 97 |
| Tear propagation resistance | N/mm | 0.41 | 0.45 | 0.38 |
| Air permeability | dm^3/s | 0.89 | 0.92 | 1.19 |
| Rebound resilience | % | 59 | 55 | 60 |
| Compression set 50% | % | 4.3 | 4.4 | 4.0 |
| Wet compression set | % | 10.1 | 9.4 | 9.4 |
| HACS 1 cycle | % | 11.3 | 12.1 | 9.4 |

Use Examples IV-VI

|  |  | Example | | |
|---|---|---|---|---|
|  |  | IV | V | VI |
| Formulation |  |  |  |  |
| Polyol from Example A | parts | 60 |  |  |
| Polyol from Example B | parts |  | 60 |  |
| Polyol from Example C | parts |  |  | 60 |
| Polyol 2 (L2048) | parts | 3 | 3 | 3 |
| Polyol 3 (L4800N) | parts | 37 | 27 | 37 |
| Dabco 33 LV | parts | 0.12 | 0.12 | 0.12 |
| Niax A 1 | parts | 0.05 | 0.05 | 0.05 |
| Diethanolamine | parts | 1.0 | 1.0 | 1.0 |
| Ortegol 204 | parts | 1.5 | 1.5 | 1.5 |
| Tegostab B 8616 | parts | 1.0 | 1.0 | 1.0 |
| Water | parts | 2.0 | 2.0 | 2.0 |
| Kosmos 29 | parts | 0.11 | 0.11 | 0.1 |
| Isocyanate 2 | index = 100 |  |  |  |
| Reaction times |  |  |  |  |
| Cream time | s | 14 | 13 | 13 |
| Fiber time | s | 115 | 115 | 110 |

-continued

|  |  | Example | | |
|---|---|---|---|---|
|  |  | IV | V | VI |
| Properties |  |  |  |  |
| Foam density | kg/m^3 | 38.0 | 36.6 | 36.7 |
| Compressive strength 25% | kPa | 2.9 | 2.8 | 2.9 |
| Compressive strength 40% | kPa | 3.6 | 3.4 | 3.5 |
| Compressive strength 65% | kPa | 7.4 | 7.0 | 7.4 |
| Hysteresis | % | 24.2 | 24.0 | 24.9 |
| Tensile strength | kPa | 93 | 83 | 88 |
| Elongation at break | % | 102 | 101 | 97 |
| Tear propagation resistance | N/mm | 0.53 | 0.59 | 0.54 |
| Air permeability | dm^3/s | 0.411 | 0.342 | 0.450 |
| Rebound resilience | % | 55 | 54 | 52 |
| Compression set 50% | % | 3.2 | 3.9 | 3.7 |
| Wet compression set | % | 10.8 | 9.9 | 13.4 |
| HACS 1 cycle | % | 4.3 | 5.5 | 5.9 |

Use, Comparative Examples

Comparative Example I

The polyol from Comparative Example B was tested both in the MDI foam formulation and in the TDI foam formulation. In both cases, very closed foams which could no longer be worked open were obtained. After cooling, the foams displayed a high degree of shrinkage. Even the customary formulation adaptations such as reduction of the gel catalyst (Dabco 33LV, tin octoate) or extra addition of the cell-opener polyol (polyol 2) produced no sensible foams.

The experimental data thus show that the polyetherols of the invention are clear and phase-stable and also display a high reactivity, for example in PU applications. In addition, the polyetherols of the invention can, in comparison with conventional (generally petrochemicals-based) polyetherols, be processed readily in PU formulations and give advantageous mechanical properties.

The invention claimed is:

1. A process for preparing a polyether polyol, the process comprising:
   reacting
   a hydroxyl-comprising fatty acid ester, a hydroxyl-modified fatty acid ester, or any mixture thereof,
   with
   a mixture of ethylene oxide and a further alkylene oxide different from ethylene oxide in the presence of a double metal cyanide catalyst in at least two process sections,
   wherein
   each process section in the at least two process sections is a phase of the process where composition of the mixture of ethylene oxide and a further alkylene oxide different from ethylene oxide remains constant for a period of at least thirty minutes, and
   the mixture in each process section has a composition different from the mixture in an immediate preceding and an immediate subsequent process section.

2. The process according to claim 1, wherein
   the hydroxyl-comprising fatty acid ester is at least one selected from the group consisting of a hydroxyl-comprising fat and a hydroxyl-comprising oil, and
   the hydroxyl-modified fatty acid ester is at least one selected from the group consisting of a hydroxyl-modified fat and a hydroxyl-modified oil.

3. The process according to claim 1, wherein the further alkylene oxide is at least one selected from the group consisting of propylene oxide, 1,2-butylene oxide, and 2,3-butylene oxide.

4. The process according to claim 1, wherein the process comprises precisely two process sections.

5. The process according to claim 1, wherein the mixture comprises precisely one further alkylene oxide different from ethylene oxide.

6. The process according to claim 1, wherein the further alkylene oxide is propylene oxide.

7. The process according to claim 1, wherein a mass ratio of ethylene oxide to a total mass of all further alkylene oxides in the mixture in a last process section is from 35:65 to 75:25.

8. The process according to claim 1, wherein a mass ratio of ethylene oxide to a total mass of all further alkylene oxides in the mixture in process sections preceding a last process section is from 35:65 to 1:99.

9. The process according to claim 1, wherein a mass ratio of ethylene oxide to a total mass of all further alkylene oxides in the mixture in a last process section is from 40:60 to 70:30.

10. The process according to claim 1, wherein a mass ratio of ethylene oxide to a total mass of all further alkylene oxides in the mixture in process sections preceding a last process section is from 30:70 to 5:95.

11. The process according to claim 1, wherein the double metal cyanide catalyst is at least one selected from the group consisting of a Co—Zn double metal cyanide catalyst, a Fe—Zn double metal cyanide catalyst, and a Ni—Zn-based double metal cyanide catalyst.

12. The process according to claim 1, wherein the double metal cyanide catalyst is a zinc hexacyanocobaltate catalyst.

* * * * *